United States Patent [19]

Zander

[11] Patent Number: 5,296,242

[45] Date of Patent: Mar. 22, 1994

[54] AQUEOUS SOLUTION AND THE USE THEREOF

[76] Inventor: Rolf Zander, Luisenstrasse 17, D-6500 Mainz, Fed. Rep. of Germany

[21] Appl. No.: 922,819

[22] Filed: Jul. 31, 1992

[30] Foreign Application Priority Data

Aug. 3, 1991 [DE] Fed. Rep. of Germany ....... 4125819

[51] Int. Cl.$^5$ .............................................. A61K 33/10
[52] U.S. Cl. .................................... 424/717; 424/715
[58] Field of Search ................................ 424/717, 715

[56] References Cited

U.S. PATENT DOCUMENTS

| | | | |
|---|---|---|---|
| 4,489,535 | 12/1984 | Veltman | 424/717 |
| 4,548,817 | 10/1985 | Filley et al. | 424/717 |
| 4,604,286 | 8/1986 | Kawajiri | 424/717 |

Primary Examiner—Allen J. Robinson
Assistant Examiner—Lambkin
Attorney, Agent, or Firm—Biebel & French

[57] ABSTRACT

A sterilizable aqueous solution with substantially physiological values of the pH, bicarbonate concentration and $CO_2$ partial pressure, as well as with metabolizable anions in the form of two separately stored single solutions, which are combined with one another prior to use and whereof one is a bicarbonate-free, acid solution and the other a bicarbonate-containing, alkaline solution, is characterized in that per liter of the finished solution obtained by combining the two single solutions, the acid single solution contains 7.3 mmole±3% of at least one metabolizable, organic acid and the alkaline single solution 19.1 mmole±3% of alkali bicarbonate and 6.1 mmole±3% of alkali carbonate.

7 Claims, No Drawings

AQUEOUS SOLUTION AND THE USE THEREOF

Bicarbonate-containing dialysis, substitution or infusion liquids for hemodialysis, peritoneal dialysis, hemofiltration or infusion are already known. Such bicarbonate-containing liquids lead to various galenic problems, particularly if they are not used immediately after preparation and are instead stored in containers.

Bicarbonate solutions are not stable, because there is always a risk that $CO_2$ escapes from a bicarbonate solution and consequently the composition of the solution changes. Certain constituents of such liquids, particularly glucose and amino acids, can only be sterilized or stored with acid pH-values in the range 5.0 to 5.5, because otherwise denaturation and/or brown colouration occurs. However, to be usable, dialysis or infusion solutions must be sterilizable. For the compensation of calcium losses, it is often necessary to supply calcium ions to dialysis patients with the dialysis solution. However, such calcium ions cannot be brought together at an alkaline pH-value with the carbonate ions, which can be formed from the bicarbonate, because otherwise insoluble calcium carbonate would precipitate.

EP-OS 161 471 discloses a two-chamber container for the storage and preparation of a bicarbonate-containing dialysis, substitution or infusion liquid, which is made from a special polymer, which separates the two chambers from one another in a liquid and gas-tight manner. One chamber contains a bicarbonate-free acid solution and the other a bicarbonate-containing alkaline solution. Prior to use the two chambers can be interconnected for mixing the contents and by means of an outlet tube the mixed solution can be supplied for its intended use.

However, the latter document does not describe the simultaneous use of alkali carbonate and alkali bicarbonate. It is in fact expressly pointed out that one of the two alkali salts is to be used. The storage container provided for such liquids is difficult and expensive to manufacture, because it must be ensured that no $CO_2$ escapes, so that the composition of the bicarbonate-containing alkaline solution does not change during storage.

The aqueous solutions described in EP-OS 161 471 do not have physiological values of the pH, the bicarbonate concentration and the $CO_2$ partial pressure. The same applies with regards to the dialysis solutions described in EP-OS 277 868. The dialysis solutions used up to now, particularly in continuous ambulatory peritoneal dialysis do not have a physiological composition, but instead, for stability reasons, always an acid pH-value, such as in the range 5.2 to 5.5. Such acid dialysis solutions can lead to damage to the peritoneum, to irritation of the defence system of the body and to pain in the abdominal cavity.

DE-OS 3 514 346 discloses liquids, particularly for the calibration of $CO_2$ analysis equipment, which in contact with the atmospheric air do not change their overall $CO_2$ content and which contain certain concentrations of alkali carbonate and alkali bicarbonate. However, in the case of these solutions it is solely a question of obtaining a liquid with a $CO_2$ partial pressure, which corresponds to that of atmospheric air, but no attempt is made to adjust physiological values of the acid—base status of said liquid.

The problem of the invention was to obtain a sterilizable, aqueous solution with physiological values of the pH, bicarbonate concentration and $CO_2$ partial pressure usable as a dialysis, substitution or infusion solution and which can be stored in air, without requiring special equipment for preventing a diffusing off or in of carbon dioxide.

According to the invention this problem is solved by an aqueous solution, which contains metabolizable anions and which is in the form of two separately stored single solutions to be combined prior to use, whereof one is a bicarbonate-free, acid solution and the other a bicarbonate-containing, alkaline solution, the aqueous solution according to the invention being characterized in that per liter of the finished solution obtained by combining the two single solutions, the acid single solution contains 7.3 mmole±3% of at least one metabolizable organic acid and the alkaline single solution 19.1 mmole±3% alkali bicarbonate and 6.1 mmole±3% alkali carbonate.

Aqueous solutions according to the invention having such a composition can be stored in air, without having to be placed in special containers preventing a diffusing off or in of $CO_2$. Thus, there is no need to use as storage containers either glass bottles or flasks, which in many cases are difficult to handle, or specially constructed gas-impermeable containers, such as are e.g. described in EP-OS 161 471. This advantage is e.g. particularly significant in the case of ambulatory peritoneal dialysis, in which it is comfortable and advantageous for the patient to be able to use a normal bag for the dialysis liquid and to be independent of glass containers.

The solutions according to the invention are sterilizable, even if they contain e.g. glucose or amino acids, because the acid, bicarbonate-free solution has a pH-value of approximately 5, which prevents denaturation or brown colouration.

The preliminary research leading to the present invention revealed that dialysis, substitution or infusion solutions are particularly suitable if their pH-value, bicarbonate concentration and $CO_2$ partial pressure corresponds to the physiological blood plasma values. These physiological values of the acid-base status are in the case of the pH value 7.40±0.05, for the bicarbonate concentration 24 mmole/l and for the $CO_2$ partial pressure 40 mm Hg. If these values are obtained in an artificially prepared aqueous solution, then on using such solutions as a dialysis, substitution or infusion solution, it is ensured that there is not overdosing or underdosing relative to the acid-base status and consequently an alkalosis or acidosis is produced, that no hyperventilation or hypoventilation occurs with respect to the breathing of a patient and at the point of application when used as an infusion solution there are no local reactions on the vein or when used as a peritoneal dialysis solution there are no local reactions on the peritoneum.

The inventive aqueous solutions quantitatively give said physiological values, so that the indicated advantages are obtained when using said aqueous solutions.

The aqueous solutions according to the invention also permit the addition of all possible desired electrolytes, such as calcium and/or magnesium ions, without there being any risk of precipitating calcium or magnesium carbonate, because these ions are added to the bicarbonate-free acid solution.

Metabolizable anions of organic acids are desired for the therapy of acidosis. In the inventive aqueous solutions these anions constitute long-term buffers, because their action is only observed after minutes to hours following administration, as a function of the reaction in the hepatic metabolism and as a function of the organic acid or acids used.

This long-term buffer effect supplements the immediate buffer effect of the bicarbonate in physiological concentration.

On combining the two single solutions, accompanied by the formation of the finished inventive solution, the metabolizable, organic acids of the acid single solution primarily quantitatively react with the carbonate ions of the alkaline single solution, because the carbonate ions have a higher pK than the bicarbonate ions. From the carbonate ions are formed bicarbonate ions, which only react in a secondary, quantitative manner with the remaining metabolizable organic acids, accompanied by the formation of $CO_2+H_2O$. This secondary reaction produces a $CO_2$ partial pressure of 40 mm Hg.

In particular the alkali carbonate, but also alkali bicarbonate are used in the solution system according to the invention in order to form the alkali salts of the added, metabolizable organic acids, which is decisive for the therapy. If the organism was in fact supplied with the organic acid, such as e.g. lactic acid, the latter dissociates completely at the physiological pH of 7.40 and consequently leads to acidosis. If it is decomposed in the metabolism, such as in the liver, $CO_2+H_2O$ are formed, i.e. neutral end products. In the case of lactic acid infusion, e.g. the pH-value immediately drops (acidosis) and is then standardized within roughly 2 hours.

However, if the alkali salt, such as sodium lactate is added to the organism, within minutes to hours and in accordance with the metabolism of the acid salt in the liver, there is an alkalization of the organism, because per mole of salt the alkali salt carries 1 mole $H^+$ into the metabolism. In the case of a lactate infusion, e.g. the pH-value initially remains neutral and then e.g. within 2 hours passes into the alkaline range.

The speed at which a metabolizable anion leads to an alkalization of the organism is dependent on the metabolic position of the liver, the nature of the anions supplied and the anion concentration.

Metabolizable, organic anions are added to the infusion solutions, in order to prophylactically initiate an alkalization of the organism. Metabolizable, organic anions are also used in dialysis solutions, in order to compensate the acidosis of the dialysis patient which increases during dialysis.

Up to now, for galenic reasons no infusion solution has contained bicarbonate, which must necessarily lead to a so-called dilution acidosis, because per liter of solution the organism must make available from its reserve 24 mmole of bicarbonate. This dilution acidosis can be detected both in vitro and in vivo.

The solutions according to the invention offer the further advantage that with respect to the metabolizable ions, whose alkalization effect is desired, no false dosing is possible, which can in turn lead to an iatrogenic alkalosis, which may represent a risk for the patient, because he must compensate this alkalosis by hypoventilation, which is limited because the reduction of breathing can produce a hypoxia (oxygen deficiency) on the part of the patient.

Thus, the inventive solutions contain the immediate buffer bicarbonate in physiological concentration, together with the long-term buffer metabolized anion in the desired concentration. Preferred metabolizable acids usable in the aqueous solutions according to the invention are pyruvic, lactic, oxalic, fumaric, acetic, malic, maleic, malonic and succinic acids.

It is also preferable to adjust the divergences of 7.3 mmole of the metabolizable acids, 19.1 mmole of the alkali bicarbonate and 6.1 mmole of the alkali carbonate per liter of finished solution to only ±1%, in order to obtain a pH-value of 7.40±0.05 and obtain divergences of the $CO_2$ partial pressure of ±4 mm Hg.

The above-indicated millimole quantities for the individual components relate to the volume of the finished solution obtained from the two single solutions by mixing, so that the volumes of the acid and alkaline single solutions can be varied at random, provided that their concentrations are adjusted in accordance with the above teaching. If e.g. the acid and alkaline single solution is in each case adjusted to 1 liter, so that the finished solution has a volume of 2 l, then in the acid solution it is necessary to have 14.6 mmole/l of the metabolizable, organic acid and in the alkaline solution 38.2 mmole/l of alkali bicarbonate and 12.2 mmole/l of alkali carbonate. On changing the volume ratios of the two single solutions the concentrations must be correspondingly converted.

When the description and claims refers to an acid and alkaline single solution, this obviously also covers the possibility of the total volume of the acid and alkaline single solution being subdivided, which however, normally leads to no additional advantage. These partial quantities of the alkaline or acid single solution can be the same or different with respect to the composition, provided that in all the partial quantities of the single solutions together the above-indicated millimoles of the indicated components are obtained.

It is also appropriate for the acid single solution to additionally contain calcium and magnesium ions. As stated, it can also additionally contain other substances, such as glucose and/or amino acids.

The aqueous solutions according to the invention completely eliminate the hitherto known problems of bicarbonate infusions. When administering bicarbonate for the therapy of an acidosis $CO_2+H_2O$. The administration of relatively high bicarbonate concentrations consequently always leads to a hyperventilation, which is unpleasant for the patient, because the necessarily formed $CO_2$ represents a breathing stimulus, which triggers the hyperventilation, for the purpose of breathing the additionally formed $CO_2$. As the inventive infusion solutions have a bicarbonate concentration of 24 mmole/l, the overdosing or incorrect dosing of bicarbonate in an infusion solution is automatically excluded.

The acid single dose can, in addition to the metabolizable organic acid or acids, also contain salts thereof, in order to obtain the desired metabolizable anion concentration.

The following tables I to III provide examples for the composition of the acid single solution in conjunction with the resulting base concentrations in the finished, combined solution following 1:1 mixing with the alkaline solution, all the details relating to 37° C. and the concentrations are given in millimole/liter.

TABLE I

Single solutions, pH = 4.0 to 6.0
Examples of the composition of the acid single solutions and the base concentrations in the finished solutions (details based on 37° C., concentrations (c) in mmole/l)

| Acid | Base | pK | Acid Single Solution | | | Finished Solution |
| | | | pH | cAcid | cBase | cBase |
| --- | --- | --- | --- | --- | --- | --- |
| Lactic acid | Lactate | 3.678 | 4.0 | 14.60 | 30.65 | 22.62 |
| Oxalic acid | Oxalate | 3.846 | 4.0 | 14.60 | 20.82 | 17.71 |

TABLE I-continued

Single solutions, pH = 4.0 to 6.0
Examples of the composition of the acid single solutions and the base concentrations in the finished solutions (details based on 37° C., concentrations (c) in mmole/l)

| Acid | Base | pK | Acid Single Solution pH | cAcid | cBase | Finished Solution cBase |
|---|---|---|---|---|---|---|
| Fumaric acid | Fumarate | 4.166 | 4.0 | 14.60 | 9.96 | 12.28 |
| Acetic acid | Acetate | 4.565 | 4.0 | 14.60 | 3.99 | 9.29 |
| Malic acid | Malate | 4.728 | 4.0 | 14.60 | 2.73 | 8.67 |
| Acetic acid | Acetate | 4.655 | 5.0 | 14.60 | 39.76 | 27.18 |
| Malic acid | Malate | 4.728 | 5.0 | 14.60 | 27.32 | 20.96 |
| Succinic acid | Succinate | 5.307 | 5.0 | 14.60 | 7.20 | 10.90 |
| Malonic acid | Malonate | 5.320 | 5.0 | 14.60 | 6.99 | 10.79 |
| Maleic acid | Maleate | 5.842 | 5.0 | 14.60 | 2.10 | 8.35 |
| Succinic acid | Succinate | 5.307 | 6.0 | 14.60 | 72.00 | 43.30 |
| Malonic acid | Malonate | 5.320 | 6.0 | 14.60 | 69.88 | 42.24 |
| Maleic acid | Maleate | 5.842 | 6.0 | 14.60 | 21.01 | 17.80 |

The pK values are measured values at 37° C. and an ionic strength of 160 mmole/l.

Results:
1. As a function of the pH-setting of the acid solution, which takes place for galenic reasons, only a limited number of organic acids can be used.
2. If the base concentration of the organic acid (metabolizable anion) is to be in a therapeutic range between approximately 10 and 50 mmole/l, based on the finished solution, only a limited pH-range can be used for the acid single solution.

TABLE II

Combination solution, pH 5.0
Example for the composition of the acid solution and the base concentrations in the finished solution, if several metabolizable organic acids or their bases (anions) are to be combined (details based on 37° C., concentration (c) in mmole/l)

| Acid | Base | pK | Acid Single Solution pH | cAcid | cBase | Finished Solution cBase |
|---|---|---|---|---|---|---|
| Fumaric acid | Fumarate | 4.166 | 5.0 | 4.867 | 33.21 | 19.04 |
| Succinic acid | Succinate | 5.307 | 5.0 | 4.867 | 2.40 | 3.63 |
| Maleic acid | Maleate | 5.842 | 5.0 | 4.857 | 0.70 | 2.78 |
|  | Sum |  | 5.0 | 14.60 | 36.31 | 25.45 |

TABLE III

Single solutions with malonic acid/malonate, pH = 4.0 to 6.0
Examples for the composition of the acid single solution and the base concentrations in the finished solution, if the same metabolizable acid or its base (anion) is to be used at different pH-values (details based on 37° C., concentration (c) in mmole/l)

| Acid | Base | pK | Acid Single Solution pH | cAcid | cBase | Finished Solution cBase |
|---|---|---|---|---|---|---|
| Malonic acid | Malonate | 5.320 | 4.0 | 14.60 | 0.7 | 7.65 |
| Malonic acid | Malonate | 5.320 | 5.0 | 14.60 | 6.99 | 10.79 |
| Malonic acid | Malonate | 5.320 | 6.0 | 14.60 | 69.88 | 42.24 |

Measurement results

Measurement of the pH-value (mean value of 10 measurements, 37° C.) before and after mixing the alkaline single solution ($HCO_3^-/CO_3^{--}$) with the acid single solution ($Na^+$, $K^+$, $Ca^{++}$, organic acid, organic base, $Cl^-$) in a ratio of 1:1 with the aim of obtaining in the finished solution pH=7.40±0.05, $cHCO_3^{31} = 24.0$ mmole/l, $cNa^+ = 140$ mmole/l, $cK^+ = 4.0$ mmole/l, $cCa^{++} = 2.5$ mmole/l (as a function of the concentration of the organic acid/base, the NaCl concentration of the acid single solution must be correspondingly adjusted).

|  | Alkaline single solution | Acid single solution | Finished solution |
|---|---|---|---|
| Solutions according to table I with a pH of 5.0: | | | |
| Acetic acid/Acetate | 9.38 | 5.07 | 7.407 |
| Malic acid/Malate |  | 4.93 | 7.395 |
| Succinic acid/Succinate |  | 5.06 | 7.393 |
| Maleic acid/Maleate |  | 4.92 | 7.409 |
| Combination solution according to Table II: | | | |
| Fumaric acid/Fumarate |  |  |  |
| Succinic acid/Succinate |  |  |  |
| Maleic acid/Maleate | 9.39 | 4.99 | 7.401 |
| Solutions according to Table III: | | | |
| Malonic acid/Malonate | 9.39 | 4.16 | 7.412 |
| Malonic acid/Malonate |  | 4.95 | 7.416 |
| Malonic acid/Malonate |  | 5.94 | *7.519 |

*Note
As the malonic acid has a relatively high pK-value (5.32) at a pH of 7.40 it leads to a minimum buffer effect if present in high concentration (here 42.24 mmole/l): $CO_2(H_2CO_3)$ is buffered in traces, so that there was a minimum pH-value rise ($pCO_2$ dropped).

The invention also relates to the use of the above-described aqueous solutions, particularly as dialysis, substitution or infusion solutions.

EXAMPLE

In the following performance example (details related to 37° C.), the alkaline single solution and acid single solution were in each case adjusted to 1 liter. The alkaline single solution contained 38.2 mmole/l of sodium bicarbonate and 12.2 mmole/l of sodium carbonate and the pH-value of the solution was 9.4.

The acid single solution contained 14.6 mmole/l of acetic acid and 39.8 mmole/l of sodium acetate and had a pH-value of 5.0.

Both solutions were completely stable in storage without using special containers preventing a diffusing in or out of $CO_2$. Their composition remained stable over long periods.

On combining the two single solutions 2 l, of finished solution was obtained with a $CO_2$ partial pressure of 40 mm Hg, a pH-value of 7.40, a bicarbonate concentration of 24.0 mmole/l and an acetate concentration of 27.2 mmole/l. This solution can be used with advantage as a dialysis, substitution or infusion solution.

I claim:

1. Sterilizable aqueous solution with substantially physiological values of the pH, bicarbonate concentration and $CO_2$ partial pressure, as well as with metabolizable anions in the form of two separately stored single solutions, which are combined with one another prior to use and whereof one is a bicarbonate-free, acid solution that is storage stable in contact with atmospheric air and the other a bicarbonate-containing, alkaline solution that is also stable in contact with atmospheric air, characterized in that per liter of the finished solution obtained by combining the two single solutions, the acid single solution contains 7.3 mmole±3% of at least one metabolizable, organic acid and the alkaline single solution 19.1 mmole±3% of alkali bicarbonate and 6.1 mmole±3% of alkali carbonate.

2. Solution according to claim 1, characterized in that, per liter of the finished solution obtained by combining the two single solutions, the acid single solution contains 7.3 mmole±1% of metabolizable, organic acids and the alkaline single solution 19.1 mmole±1% of alkali bicarbonate and 6.1 mmole±1% of alkali carbonate.

3. Solution according to claim 1, characterized in that the acid single solution additionally contains at least one alkali salt of at least one metabolizable organic acid.

4. Solution according to claim 3, characterized in that it contains sodium salts of metabolizable, organic acids.

5. Solution according to any one of the claim 1, characterized in that it contains as the alkali bicarbonate sodium bicarbonate and as the alkali carbonate sodium carbonate.

6. Solution according to claim 1, characterized in that the acid single solution additionally contains calcium and/or magnesium ions.

7. Solution according to claim 1, characterized in that it contains as metabolizable, organic acids pyruvic, lactic, oxalic, fumaric, acetic, succinic, malic, maleic and/or malonic acid.

* * * * *